United States Patent [19]
Wasserman et al.

[11] Patent Number: 5,834,588
[45] Date of Patent: Nov. 10, 1998

[54] (CYANOMETHYLENE) PHOSPHORANES AS CARBONYL 1,1-DIPOLE SYNTHONS FOR USE IN CONSTRUCTING COMBINATORIAL LIBRARIES

[75] Inventors: Harry H. Wasserman, New Haven, Conn.; Wen-Bin Ho, Los Altos, Calif.

[73] Assignee: Yale University, New Haven, Conn.

[21] Appl. No.: 503,070

[22] Filed: Jul. 14, 1995

[51] Int. Cl.$^6$ ................................ C07K 1/02; C07F 9/535
[52] U.S. Cl. ........................... 530/340; 530/333; 530/338; 568/9
[58] Field of Search ..................................... 530/333, 338, 530/340

[56] References Cited

PUBLICATIONS

"Cyanomethylene)phosphoranes as Novel Carbonyl 1,1-Dipole Synthons: An Efficient Synthesis of α–Keto Acids, Esters, and Amides", Harry H. Wasserman and Wen–Bin Ho, J. Organic Chemistry, 1994, 59, 4364–4366.

Wasserman et al, J. Org. Chem., 58 (18), 4785–4787, 1993), Sep. 1993.

*Primary Examiner*—Cecilia J. Tsang
*Assistant Examiner*—Michael Borin
*Attorney, Agent, or Firm*—Pennie & Edmonds LLP

[57] ABSTRACT

The invention is directed to systematic synthetic and testing strategies for α-keto acids, esters and amides. The method of synthesis comprises (A) reacting (cyanomethylene) triphenylphosphorane with a carbonyl compound selected from carboxylic acids (RCOOH) and acyl chlorides (RCOCl) to make a cyano keto phosphorane, (B) oxidizing said phosphorane and (C) reacting the oxidized product with a nucleophile (NuH) to make the product α-keto acid, ester or amide. Systematic synthesis and testing are achieved by a modular approach in which arrays of molecules are generated by variation of R and Nu.

6 Claims, No Drawings

(CYANOMETHYLENE) PHOSPHORANES AS CARBONYL 1,1-DIPOLE SYNTHONS FOR USE IN CONSTRUCTING COMBINATORIAL LIBRARIES

FIELD OF THE INVENTION

The present invention relates to α-keto acids, esters and amides, and a method for synthesizing them. The present invention further relates to a method for the modular development of (cyanomethylene)phosphorane-derived synthetic organic molecules, possessing selected properties for a particular application. This method involves: a) the synthesis of an array of different molecules generated from base modules of (cyanomethylene)phosphorane-derived molecules containing a chosen set of substituent groups which confer structural diversity; and/or the reaction of these modules with other appropriate reactive groups to produce an array of molecules possessing a chosen set of diverse structural moieties; and, b) the screening of some or all of the molecules in the array for the desired set of properties in a target application. The iterative application of this method enables molecules to be produced, having an optimum balance of properties for the particular application.

BACKGROUND OF THE INVENTION

The discovery of new molecules has traditionally focused in two broad areas, biologically active molecules, which are used as drugs for the treatment of life-threatening diseases, and new materials, which are used in commercial, and especially, in high technological applications. In both areas, the strategy used to discover new molecules has involved two basic operations: (i) a more or less random choice of a molecular candidate, prepared either via chemical synthesis or isolated from natural sources; and, (ii) the testing of the molecular candidate for the property or properties of interest. This discovery cycle is repeated indefinitely until a molecule possessing the desirable property, i.e., "lead molecule", is located. This "lead molecule" discovery process has been inherently ad hoc in nature and is time-consuming, laborious, unpredictable and costly.

Once a candidate lead molecule has been determined, the synthetic chemist must subsequently find ways to synthesize structural variants of this molecule to optimize its properties in the desired application. In the case where the lead molecule is a synthesized organic species or a natural product, the chemist is usually limited to certain structural and synthetic reaction schemes. These schemes are dictated largely by the structural composition of the lead molecule and by the requirements of the specific application. For example, in cases where the lead molecule possesses a functionally important aromatic ring, various electrophilic and nucleophilic substitutions may be carried out on the ring to produce variants. Each such case must be approached as a specific independent design and synthesis problem, starting each time from the beginning, because of the lack of availability of an appropriate chemistry to simply alter the structure of the lead compound to produce the variant.

Recently, some attempts have been made to modularize certain synthetic organic reaction schemes to facilitate modification and transformation of a lead or base compound (see, for example, 1993 *Proc. Natl. Acad. Sci. USA,* 90, 6909). However, the molecules which can be produced by such attempts are extremely limited in their achievable diversity and are still bounded by factors dictated by the choice of specific structural themes. In the case where the "lead molecule" is a naturally occurring, biological molecule, such as a peptide, a protein, an oligonucleotide or a carbohydrate, simple synthetic point-modifications to the lead molecule to produce variants are quite difficult to achieve.

A brief account of the strategies and tactics used in the discovery of new molecules is described below. The emphasis is on biologically interesting molecules; however, the technical problems encountered in the discovery of biologically active molecules as outlined here are also illustrative of the problems encountered in the discovery of molecules which can serve as building blocks for the development of new tools and materials for a variety of high technological applications. Furthermore, as discussed below, these problems are also illustrative of the problems encountered in the development of fabricated structures and materials for high technological applications.

The present invention is directed to systematic synthetic and testing strategies for α-keto acids, esters and amides, compounds which are known to be of use as protease inhibitors active against leukotriene A4 hydrolase, chimase and human immunodeficiency virus (HIV). (see for example W. Yuan et al., 1994, *J. Am. Chem. Soc.* 114:6552; B. Munoz, et al., 1994 *Bioorganic & Medicinal Chemistry* 2:1085–1089; S. Mehdi, 1993 *Bioorganic Chemistry* 21:249–259)

Drug Design

Modern theories of biological activity state that biological activities, and therefore physiological states, are the result of molecular recognition events. For example, nucleotides can form complementary base pairs so that complementary single-stranded molecules hybridize resulting in double- or triple-helical structures that appear to be involved in regulation of gene expression. In another example, a biologically active molecule, referred to as a ligand, binds with another molecule, usually a macromolecule referred to as ligand-acceptor (e.g., a receptor, an enzyme, etc.), and this binding elicits a chain of molecular events which ultimately gives rise to a physiological state, e.g., normal cell growth and differentiation, abnormal cell growth leading to carcinogenesis, blood-pressure regulation, nerve-impulse-generation and -propagation, etc. The binding between ligand and ligand-acceptor is geometrically characteristic and extraordinarily specific, involving appropriate three-dimensional structural arrangements and chemical interactions.

A currently favored strategy for the development of agents which can be used to treat diseases involves the discovery of forms of ligands of biological receptors, enzymes, or related macromolecules, which mimic such ligands and either boost, i.e., agonize, or suppress, i.e., antagonize, the activity of the ligand. The discovery of such desirable ligand forms has traditionally been carried out either by random screening of molecules (produced through chemical synthesis or isolated from natural sources), or by using a so-called "rational" approach involving identification of a lead-structure, usually the structure of the native ligand, and optimization of its properties through numerous cycles of structural redesign and biological testing. Since most useful drugs have been discovered not through the "rational" approach but through the screening of randomly chosen compounds, a hybrid approach to drug discovery has recently emerged which is based on the use of combinatorial chemistry to construct huge libraries of randomly-built chemical structures which are screened for specific biological activities. (S. Brenner and R. A. Lerner, 1992, *Proc. Natl. Acad. Sci. USA* 89:5381)

Most lead-structures which have been used in the "rational" drug design approach are native polypeptide ligands of receptors or enzymes. The majority of polypeptide ligands, especially the small ones, are relatively unstable in physiological fluids, due to the tendency of the peptide bond to undergo facile hydrolysis in acidic media or in the presence of peptidases. Thus, such ligands are decisively inferior in a pharmacokinetic sense to non-peptidic compounds, and are not favored as drugs. An additional limitation of small peptides as drugs is their low affinity for ligand acceptors. This phenomenon is in sharp contrast to the affinity demonstrated by large, folded polypeptides, e.g., proteins, for specific acceptors, e.g., receptors or enzymes, which can be in the sub-nanomolar range. For peptides to become effective drugs, they must be transformed into non-peptidic organic structures, i.e., peptide mimetics, which bind tightly, preferably in the nanomolar range, and can withstand the chemical and biochemical rigors of coexistence with biological tissues and fluids.

Despite numerous incremental advances in the art of peptidomimetic design, no general solution to the problem of converting a polypeptide-ligand structure to a peptidomimetic has been defined. At present, "rational" peptidomimetic design is done on an ad hoc basis. Using numerous redesign-synthesis-screening cycles, peptidic ligands belonging to a certain biochemical class have been converted by groups of organic chemists and pharmacologists to specific peptidomimetics; however, in the majority of cases, results in one biochemical area, e.g., peptidase inhibitor design using the enzyme substrate as a lead, cannot be transferred for use in another area, e.g., tyrosine-kinase inhibitor design using, the kinase substrate as a lead.

In many cases, the peptidomimetics that result from a peptide structural lead using the "rational" approach comprise unnatural alpha-amino acids. Many of these mimetics exhibit several of the troublesome features of native peptides (which also comprise alpha-amino acids) and are, thus, not favored for use as drugs. Recently, fundamental research on the use of non-peptidic scaffolds, such as steroidal or sugar structures, to anchor specific receptor-binding groups in fixed geometric relationships have been described (see for example Hirschmann, R. et al., 1992 *J. Am. Chem. Soc.,* 114:9699–9701; Hirschmann, R. et al., 1992 *J. Am. Chem. Soc.,* 114:9217–9218); however, the success of this approach remains to be seen.

In an attempt to accelerate the identification of lead-structures, and also the identification of useful drug candidates through screening of randomly chosen compounds, researchers have developed automated methods for the generation of large combinatorial libraries of peptides and certain types of peptide mimetics, e.g., "peptoids", which are screened for a desirable biological activity. For example, the method of H. M. Geysen, (1984 *Proc. Natl. Acad. Sci. USA* 81:3998) employs a modification of the Merrifield peptide synthesis, wherein the C-terminal amino acid residues of the peptides to be synthesized are linked to solid-support particles shaped as polyethylene pins; these pins are treated individually or collectively in sequence to introduce additional amino-acid residues forming the desired peptides. The peptides are then screened for activity without removing them from the pins. Houghton, (1985, *Proc. Natl. Acad. Sci. USA* 82:5131; and U.S. Pat. No. 4,631,211) utilizes individual polyethylene bags ("tea bags") containing C-terminal amino acids bound to a solid support. These are mixed and coupled with the requisite amino acids using solid phase synthesis techniques. The peptides produced are then recovered and tested individually. Fodor et al., (1991, *Science* 251:767) described light-directed, spatially addressable parallel-peptide synthesis on a silicon wafer to generate large arrays of addressable peptides that can be directly tested for binding to biological targets. These workers have also developed recombinant DNA/genetic engineering methods for expressing huge peptide libraries on the surface of phages (Cwirla et al., 1990, *Proc. Natl. Acad. Sci. USA* 87:6378).

In another combinatorial approach, V. D. Huebner and D. V. Santi (U.S. Pat. No. 5,182,366) utilized functionalized polystyrene beads divided into portions each of which was acylated with a desired amino acid; the bead portions were mixed together, then divided into portions each of which was re-subjected to acylation with a second desirable amino acid producing dipeptides, using the techniques of solid phase peptide synthesis. By using this synthetic scheme, exponentially increasing, numbers of peptides were produced in uniform amounts which were then separately screened for a biological activity of interest. Another method of producing libraries of organic compounds based on dipeptides, hydantoins and benzodiazepines using a polystyrene based solid support is described by DeWitt et al. (1993, *Proc. Natl. Acad. Sci. USA,* 90:6909). Bunin et al. (1992, *J. Am. Chem. Soc.,* 114:10997) describe a method for the combinatorial synthesis of large libraries of peptides. According to Bunin, 2-amino benzophenones are attached to a polystyrene solid support and converted into various 1,4 benzodiazepine derivatives, which can then be screened for specific receptor or enzyme activity.

Zuckerman et al., (1992, *Int. J. Peptide Protein Res.* 91:1 and 1993, *Structural Biology* 3:580) also have developed similar methods for the synthesis of peptide libraries and applied these methods to the automation of a modular synthetic chemistry for the production of libraries of, for example, N-alkyl glycine peptide derivatives, called "44 peptoids", which are screened for activity against a variety of biochemical targets. (See also, Symon et al., 1992, *Proc. Natl. Acad. Sci. USA* 89:9367). Encoded combinatorial chemical syntheses have been described recently (S. Brenner and R. A. Lerner, 1992, *Proc. Natl. Acad. Sci. USA* 89:5381).

The focus of these structural diversity activities on peptide synthesis chemistry is a direct result of the fact that the ability to generate structural diversity requires, as its starting point, the access to practical stepwise sequential synthesis chemistries which allow the incorporation of varied structural elements with orthogonal reactivities. To date, these have only been worked out for the Merrifield synthesis of peptides and the Carruthers synthesis of oligonucleotides. Thus, there remains a need for an improved method for the structure-directed generation and screening of organic compounds to determine which may be suitable in a particular application.

SUMMARY OF THE INVENTION

The present invention relates to certain α-keto acids, esters and amides, and a method for making them. The method of synthesis comprises:

(A) reacting (cyanomethylene)triphenylphosphorane (1) with a carbonyl-containing compound (2) selected from the group consisting of carboxylic acid of formula RCOOH, acid anhydride derived therefrom and acyl chloride of formula RCOCl to make the corresponding cyano keto phosphorane (3);

(B) oxidizing said cyano keto phosphorane to make an α-ketoacyl cyanide (4); and (C) reacting said α-ketoacyl cyanide with a nucleophile of formula NuH to form a ketone-containing product (6).

This method is schematically depicted below:

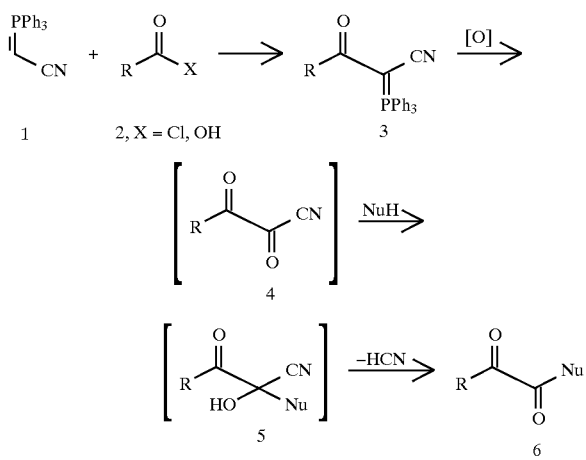

wherein
R is a structural diversity element selected from the group consisting of alkyl, cycloalkyl, substituted and unsubstituted aryl, heteroaryl, heteroatom-substituted alkyl and cycloalkyl, amidyl, peptidyl and alkoxyl; and Nu is a structural diversity element selected from the group of nucleophiles NuH consisting of amines (including hydrazines and primary and secondary amines), amino acids, peptides, peptidyl residues, water, $H_2S$, alcohols and thiols. The symbol [O] indicates oxidation, including oxidation by $O_3$ (ozone).

The present invention further relates to a method for obtaining compounds having selected properties for a particular application by forming base modules having at least two structural diversity elements. Such base modules are formed by the synthesis of a first reactive molecule, a cyano keto phosphorane, by reacting (cyanomethylene) triphenylphosphorane with an acyl chloride or carboxylic acid containing a structural diversity element R. This first reactive molecule, the cyano keto phosphorane, undergoes ready oxidation to the highly electrophilic vicinal diketo nitrile, which can be reacted with a second reactive molecule, the nucleophile NuH, in which Nu represents a the structural diversity element Nu. Sets of cyano keto phosphoranes and nucleophiles can be reacted to produce a first array of molecules in which at least one of the structural diversity elements of the compounds is varied when producing the base modules. This array can be screened to determine a first suitable compound for a particular application.

If desired, this method can be repeated by producing a second array of molecules through the formation of base modules having structural diversity elements that are different from those of the first array of molecules, and screening the second array of molecules to determine a second suitable compound for the particular application. The second array can be produced by forming base modules having at least two structural diversity elements in the same manner as the first array, except that the structural diversity elements are modified from those of the first suitable compound. The steps of producing and screening an array of molecules can be repeated as often as necessary to achieve an optimum compound for the particular application.

Advantageously, the first structural diversity element R is present in a carboxylic acid of formula RCOOH (or anhydride derived therefrom) or acyl chloride of formula RCOCl. Acids can include benzoic acid, cyclohexyl carboxylic acid, 2-thiophene carboxylic acid and nicotinic acid. Exemplary acids include Cbz-HN-$(CH_2)_{11}$-COOH, HO-$(CH_2)_{11}$-COOH, the peptide Boc-Phe-OH, the dipeptide Cbz-Gly-Gly-OH, the tripeptide, Cbz-Ala-Gly-Gly-OH. The second structural diversity element Nu is present in a nucleophile of formula NuH. Exemplary Nu units are OH, O-alkyl (including O-methyl), SH, S-alkyl (including S-methyl), Phe-OEt, or Leu-OMe.

The various base compounds represent another aspect of the present invention. New compositions made by the present invention include 2,3-dione-oxacyclotetradecane [compound (45a) described in Example 5, CAS 158299-95-7], 13-hydroxy-2-oxo-tridecanoic acid, methyl ester [compound (36a) described in Example 2, CAS 158299-87-7], 2-oxo-13-[[(phenylmethoxy)carbonyl]amino]tridecanoic acid, methyl ester [compound (23) described in Example 6, CAS 158299-99-86-6], N-[3-[[1,1-dimethylethoxy] carbonyl]amino]-1,2-dioxo-4-phenylbutyl]-L-phenylalanine [compound (41) described in Example 3, CAS 158299-91-3], 2-oxo-3-[[[[(phenylmethoxy)carbonyl] amino]acetyl]amino]-propanoic acid, methyl ester [compound (27) described in Example 8] and 2-oxo-N-[N-[N-(phenylmethoxy)carbonyl]-L-alanyl]glycyl]-β-alanine, methyl ester.

This method is useful for a wide variety of applications, including the development of new biopharmaceutical agents, new monomeric species for the modular construction of separations tools, including, chiral selectors, industrial detergents and additives, and for the development of modular chemical intermediates for the production of new materials and polymers. Specifically, the method relates to the selection of molecular modules containing appropriate structural diversity and reactivity elements, the connecting of these modules together via facile high-yield addition reactions which produce discrete, highly pure molecules in microscopic (less than or equal to 1 milligram) to macroscopic quantities (greater than 1 milligram) in a manner such that the properties of these molecules are determined by the contributions of the individual building modules. The molecular modules of the invention may be chiral, and can be used to synthesize new compounds, structures and materials which are able to recognize biological receptors, enzymes, genetic materials, and other chiral molecules, and are thus of great interest in the fields of biopharmaceuticals, separation industrial and materials science.

The present method of synthesis, with only three steps (A, B, and C), which preferably can be combined to two steps (A, B/C) is an improvement over the five step synthesis of the prior art (see for example B. Munoz, et al., 1994 *Bioorganic & Medicinal Chemistry* 2:1085.)

DETAILED DESCRIPTION OF THE INVENTION

For the purposes of this invention the following terms are defined to clearly delineate the scope of the present invention.

"Compartments" is defined as any structure in, or on which a discrete amount of a compound is situated. This term is considered to encompass structures which have classically been considered to be compartments such as sample vials and test tubes, as well as nontraditional compartments, such as, for example, silicon wafers, gelatin, polystyrene or other macromolecular media.

A base module is a set of molecules which is common to a group of larger molecules in an array of said larger molecules, where said larger molecules have one or more structural diversity elements. The term "base module" is equivalent to the term "molecular scaffolding" for the present invention.

Structural diversity elements are any organic or inorganic atom(s), molecule(s), or bond(s) which adds to or changes the structure of a base module.

A reactive group is a molecule(s) capable of forming a structural diversity element.

When a numerical variable is specified as a part of any structure or formula, such numerical variable is intended to represent each embodiment of the subject structure or formula that would correspond to each numerical value that said variable could be.

Herein, there is interest in the formation of various peptidyl α-keto esters and α-keto amides through the method depicted below:

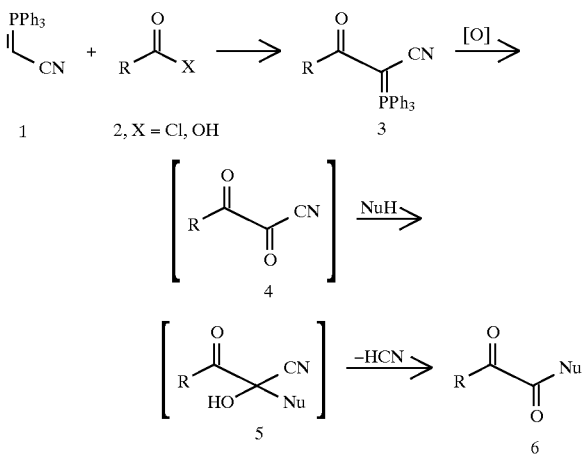

In this reaction sequence, the cyano ylide 1 may be viewed as a carbonyl 1,1-dipole synthon equivalent reacting first as a nucleophile and then, after oxidation of the carbon phosphorus double bond in the ylide intermediate, as a powerful electrophile. H. Wasserman, 1994 *J. Org. Chem.* 59:4364. The specific chemistry of these molecules, as well as an identification of the structural diversity elements and reactivity groups, follows.

Carboxylic Acids; Acyl Chlorides

The first reactive molecule, the cyano keto phosphorane, is made by reacting (cyanomethylene)triphenylphosphorane (1) with a carboxylic acid or an acyl chloride:

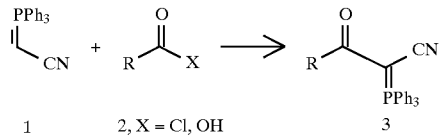

Preferred carboxylic acids include amino acids and peptides. Carboxylic acid anhydrides derived from the carboxylic acid may also be used.

Oxidation; Reaction with Nucleophile

The cyano keto phosphorane is oxidized, preferably with $O_3$ [ozone] and subsequently combined with a second reactive molecule, a nucleophile NuH:

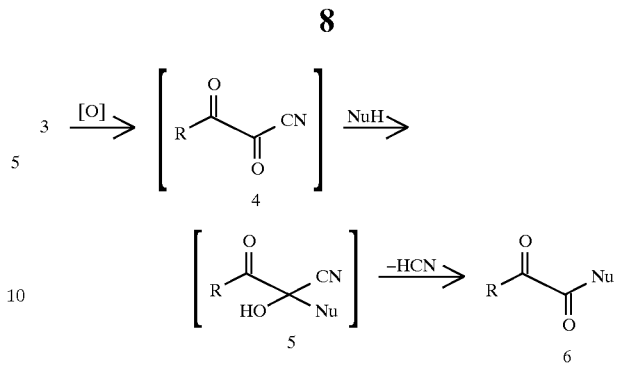

Because of the instability to isolation of compound 4, it is preferred to add the nucleophile NuH in situ, without separating compound 4 from the oxidation reaction mixture. Preferred nucleophiles include amines, amino acids, peptides, hydrazines, alchohols and thiols. Other oxidants may be used, including TBA oxone®. TBA oxone® oxidized compound 3 (R=phenyl) to intermediate compound 4 (R=phenyl).

The ability of these various reactions to be carried out in a stepwise sequential process using modules chosen in a structure-directed manner allows the production of structurally directed thematic diversity libraries, having, structural elements systematically varied around a basic motif.

The present invention is able to generate a number of different molecules for screening purposes by first forming a base module that contains at least two structural diversity elements attached thereto. These modules are formed by reacting first and second compounds, each of which has at least one structural diversity element and a reactive group. The reactive groups of the first and second compounds are such that they react with each other to form the base module by an additional reaction. By fixing one of the positions and structures of the structural diversity elements and by varying at least one of the others, an array of different molecules is easily-generated. These molecules can then be screened to determine which are suitable for a particular application or target use. Once a suitable compound is identified, it can be selected for generating a further array of molecules. This is done by modifying the particular structural diversity elements that are found to be suitable, or by combining the chosen structural diversity element with an expanded or different set of second compounds or elements. This process can be repeated as often as necessary to develop the optimum compound for the particular use.

The particular base module chosen for use in accordance with the present invention is not critical and can be any one of a wide variety of structures. Knowledge of the base modules can be represented in the form of combinatorial libraries.

From the foregoing, it is seen that various arrays of molecules can be prepared. These arrays can be generated in the desired size to facilitate the screening of a large number of molecules at one time. The arrays may be spatially arranged. For example, standard arrays having 96 compartments in an 8×12 array can be used where any number of compartments contain different molecules, while the other can contain controls or duplicate samples. It is possible, and preferred, to include 16 controls and 80 different samples in the array. After an initial screening identifies molecules having certain beneficial or desirable properties, a second tray containing, e.g., 20 samples of each of 4 different molecules, again with 16 controls, samples, can be used to confirm the original results. The samples can be placed in columns of the same material, or a completely random array can be generated to have a completely blind analysis.

In view of these variations, one of ordinary skill in the art understands that any m×p array of molecules can be generated, where m and p are integers, m being greater than 0 (zero) and p being greater than 1. There is no upper limit to m and p other than the capabilities of the testing or screening equipment. As noted above, an 8×12 array would be typical, but q compounds can be tested from arrays where m or p is as high as 25 or more; q being an integer from 1 up to the total of m times p. At this time, it is specifically preferred that m and p be integers of between 3 and 15, and that a few control molecules be included so that q is less than the product of m and p. However, this invention contemplates that use of any integer for m or p, with each integer or combination of m×p integers relied upon as representing a useful embodiment. Thus, q may be an integer equal to 1 up to the product of m multiplied by p.

As noted above, the molecules used in the array would be generated from one or more of the base molecules described herein. In this manner, combinatorial libraries of r different compounds, where r is any integer, can be made. Typically, r will be greater than 5, often 25 or greater. As noted, r can be as high as 80 or 96 using available trays, or can even be higher using specifically designed trays. Although for convenience, linear arrays are described, the specific arrangement of the molecules and tray compartments can be circular, staggered or in any other configuration which can be analyzed by the testing or screening device used.

As used herein, substituted and unsubstituted aryl groups means a hydrocarbon ring, bearing, a system of conjugated double bonds, usually comprising, an even number of 6 or more pi-bond electrons. Examples of aryl groups include, but are not limited to, phenyl, naphthyl, anisyl, toluyl, xylenyl and the like. According to the present invention, aryl also includes aryloxy, aralkyl, aralkyloxy and heteroaryl groups, e.g, pyrimidine, morpholine, piperazine, piperidine, benzoic acid, toluene or thiophene and the like. These aryl groups may also be substituted with any number of a variety of functional groups. In addition to the functional groups described above in connection with substituted alkyl groups and carbocyclic groups, functional groups on the aryl groups can be nitro groups.

As mentioned above, these structural moieties can also be any combination of alkyl, carbocyclic or, aryl, groups, for example, 1-cyclohexylpropyl, benzylcyclohexylmethyl, 2-cyclohexylpropyl, 2,2-methylcyclohexylpropyl, 2,2-methylphenylpropyl, 2,2-methylphenylbutyl, and the like.

In one preferred embodiment of the present invention one or more of the structural diversity elements, R or Nu, are reactive groups that are capable of further reactions to produce a base module. For example, the present invention is directed to structural diversity groups that may themselves be capable of further reaction to form base modules as described herein.

Orthogonal Reactivities

A key element of the present method is the presence of at least two compounds, each having a reactive group capable of forming an addition compound with the other and carrying at least one of the structural diversity groups. These compounds are used to form the base modules. These compounds may take the form of either a) multiple reactive groups which are capable of being "turned on" independently of each other, or b) groups with multiple states with differing reactivities which may be addressed or brought into being at different times or under different conditions in a reaction sequence. It is highly desirable, although not absolutely necessary, that each individual reaction be a high-yielding addition reaction without possible interfering side-reactions, so that isolation and purification steps are not necessary, or, at least, are held to a minimum.

EXAMPLES

In order to exemplify the results achieved using the methods and compounds of the present invention, the following examples are provided without any intent to limit the scope of the instant invention to the discussion therein, all parts and percentages are by weight unless otherwise indicated.

The following schematic illustrates how EDCI [1-(3-(Dimethylaminopropyl)-3-ethylcarbodiimide] and DMAP [4-dimethylaminopyridine] and O₃ [ozone] may be advantageously used:

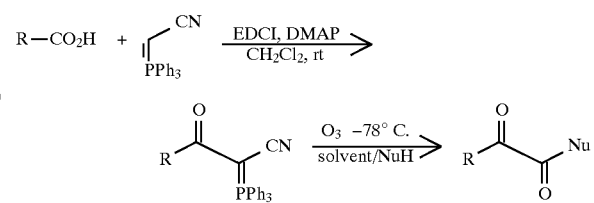

The following schematic depicts specific embodiments:

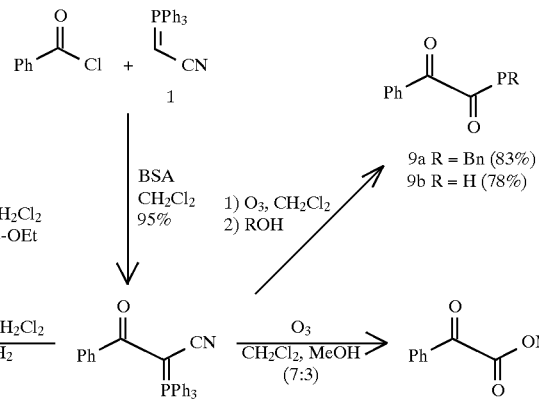

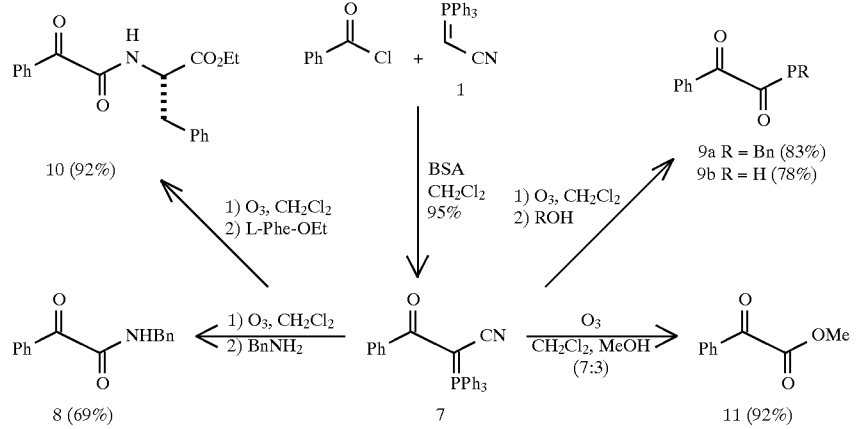

In the following, further details of specific examples are given.

EXAMPLE 1

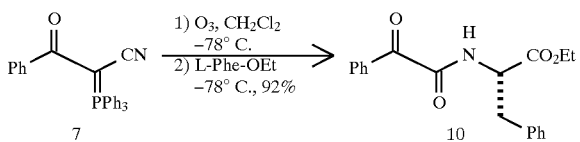

4,5-Dioxo-3-aza-2-phenylmethyl-benzenepentanoic Acid, Ethyl Ester (10):

A solution of cyano keto phosphorane 7 (200 mg, 0.49 mmol) in 5 ml of $CH_2Cl_2$ was treated with $O_3$ at $-78°$ C. until the color of the solution remained yellow-blue. The mixture was then purged with $N_2$ at $-78°$ C. until the blue color faded. To this yellow solution was added slowly a solution of (L)-Phe-OEt (prepared by treatment of Phe-OEt HCl salt (170 mg, 0.74 mmol) with $K_2CO_3$ in $H_2O$ and then extracted with ether) in 1 mL of $CH_2Cl_2$ and the resulting solution was stirred at $-78°$ C. for 1 hour. After warming up to room temperature, the solvent was evaporated and the residue was purified by flash chromatography over silica gel, eluting with (3/1) hexanes-EtOAc to afford the α-keto amide (10) (146 mg, 0.45 mmol) in 92% yield as an oil.

$R_f$ 0.56 (2/1) hexanes-EtOAc $[α]_D$ +62.7° (c 1.1, $CHCl_3$)

IR (neat) 3300, 1740, 1685, 1665, 1520, 1270, 1210 cm$^{-1}$ $^1$H NMR (300 MHz, $CDCl_3$) δ 8.25-7.19 (m, 10H, Ph), 4.96-4.81 (m, 1H, CH), 4.21 (q, J=7.2 Hz, 2H, Et), 3.3-3.12 (m, 2H, $CH_2$), 1.26 (t, J=7.2 Hz, 3H, Et)

$^{13}$C NMR (75 MHz, $CDCl_3$) δ 186.9, 170.6, 161.3, 135.4, 134.4, 133.0, 131.1, 129.3, 128.8, 128.6, 128.5, 127.6, 127.2, 61.8, 53.3, 38.0, 14.1

MS (EI) 325 (M$^+$), 252, 220, 176, 148, 146, 105

HRMS (CI): calcd for $C_{19}H_{19}NO_4$ (M+1)$^+$ 326.1292; found 326.1409

EXAMPLE 2

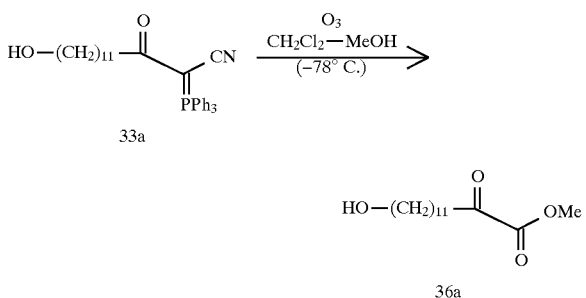

Methyl α-Keto-ω-hydroxydecanoate (36a) [also named 13-hydroxy-2-oxo-tridecanoic acid, methyl ester]:

A solution of cyano keto phosphorane 33a (70 mg, 0.14 mmol) in 20 mL of (7/3)-$CH_2Cl_2$/MeOH was treated with ozone at $-78°$ C. until the color of the solution remained blue. The mixture was then purged with $N_2$ to colorless at room temperature. The solvent was evaporated and the residue was chromatographed over silica gel, eluting with (1/1)-hexanes/EtOAc to afford the α-keto ester 36 (32 mg, 0.12 mmol) in 86% yield.

$R_f$ 0.38 (1/1) EtOAc-hexanes

IR (neat) 3280, 1735, 1460, 1280, 1065 cm$^{-1}$ $^1$H NMR (300 MHz, $CDCl_3$) δ 3.83 (s, 3H, OMe), 3.60 (t, J=6.5 Hz, 2H, $CH_2$), 2.79 (t, J=7.3 Hz, 2H, $CH_2$), 1.7-1.2 (m, 18H)

$^{13}$C NMR (75 MHz, $CDCl_3$) δ 194.3, 161.6, 63.0, 52.9, 39.3, 32.8, 29.5, 29.4, 29.36, 29.32, 29.2, 28.9, 25.7, 22.9

HRMS (EI) calcd for $C_{14}H_{27}O_4$ (M$^+$) 259.1909, found 259.1916

EXAMPLE 3

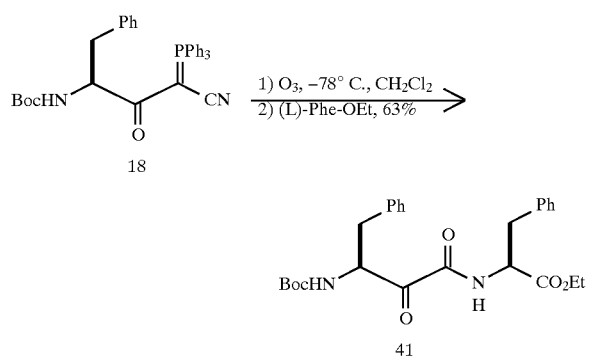

6-[[1,1-Dimethylethyloxy)carbonyl]amino]-4,5-dioxo-3-aza-2-phenylmethylbenzeneheptanoic Acid, Ethyl Ester (41) [also named N-3-[[1,1-dimethylethoxy]carbonyl]amino-1,2-dioxo-4-phenylbutyl]-L-phenylalanine, ethyl ester]:

A solution of cyano keto phosphorane (18) (200 mg, 0.37 mmol) in 4 mL of $CH_2Cl_2$ was treated with $O_3$ at $-78°$ C. until the color of the solution remained yellow-blue. The mixture was then purged with $N_2$ at $-78°$ C. until the blue color faded. To this yellow solution was added slowly a solution of (L)-Phe-OEt (prepared by treatment of Phe-OEt HCl salt (126 mg, 0.55 mmol) with $K_2CO_3$ in $H_2O$ and then extracted with ether) in 1 mL of $CH_2Cl_2$ and the resulting solution was stirred at $-78°$ C. for 1 hour. After warming up to room temperature, the solvent was evaporated and the residue was purified by flash chromatography over silica gel, eluting with (2/1) hexanes-EtOAc to afford the α-keto amide 41 (107 mg, 0.23 mmol) in 63% yield as a semisolid product. The anhydrous product can be crystallized from hexanes/ether solvent system.

$R_f$ 0.62 (tailed) (1/1) EtOAc-hexanes mp 94°–96° C.

IR (film) 3360, 1750-1675 (br), 1500, 1370, 1250, 1170, 1030 cm$^{-1}$ $^1$H NMR (300 MHz, $CDCl_3$) δ 7.3-7.0 (m, 10H, Ph), 5.35 (br s, 1H, NH), 5.03 (br s, 1H, NH), 4.88 (m, 1H, CH), 4.22 (q, J=7.3 Hz, 2H, Et), 4.15 (m, 1H, CH), 3.30-3.02 (m, 4H, 2 CH2), 1.49 (s 9H, Bu), 1.27 (t, J=7.1 Hz, 3H, Et)

$^{13}$C NMR (75 MHz, $CDCl_3$) δ 196.0, 170.3, 158.4, 154.6, 135.5, 135.4, 129.4, 129.2, 129.1, 128.6, 128.5, 127.2, 126.9, 79.9, 61.8, 56.4, 53.1, 38.0, 37.4, 28.2, 14.0

HRMS (FAB) $C_{26}H_{32}N_2O_6$ calcd for (M+Na)$^+$ 491.2158, found 491.2149

EXAMPLE 4

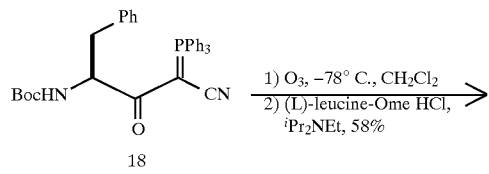

EXAMPLE 4 (continued)

6-[[(1,1-Dimethylethyloxy)carbonyl]amino]-4,5-dioxo-3-aza-2-(2-methylpropyl)-benzeneheptanoic Acid, Methyl Ester (42):

A solution of cyano keto phosphorane 18 (200 mg, 0.37 mmol) in 4 mL of $CH_2Cl_2$ was treated with $O_3$ at −78° C. until the color of the solution remained yellow-blue. The mixture was then purged with $N_2$ at −78° C. until the blue color faded. To this yellow solution was added slowly a solution of (L)-Leu-OMe HCl salt (73 mg, 0.40 mmol) and a Hunig base (0.57 mg, 0.44 mmol) in 1 mL of $CH_2Cl_2$ and the resulting solution was stirred at −78° C. for 1 hour. After warming up to room temperature, the solvent was evaporated and the residue was purified by flash chromatography over silica gel, eluting with (2/1) hexanes/-EtOAc to afford the α-keto amide 42 (89 mg, 0.21 mmol) in 58% yield as a semisolid product. The anhydrous product can be crystallized from a petroleum ether/ether solvent system.

$R_f$ 0.39 (tailed) (1/2) EtOAc-hexanes mp 149°−151° C.

IR (film) 3360, 3310, 1750, 1675, 1530, 1275, 1250, 1165 $cm^{-1}$ $^1$H NMR (300 MHz, $CDCl_3$) δ 7.8-7.1 (m, 7H, Ph, 2 NH), 5.09 (d, J−7.3 Hz, 1H), 4.63 (m, 1H), 3.98 (m, 1H), 3.76 (s, 3H, OMe), 3.15 (dd, J=13.6, 12.1 Hz, 1H), 2.64 (dd, J=13.9, 2.8 Hz, 1H), 1.67 (m, 2H), 1.42 (s, 9H, Bu), 0.94 (m, 6H, 2 Me)

$^{13}$C NMR (75 MHz, $CDCl_3$) δ 196.0, 171.9, 165.1, 158.5, 136.9, 129.1, 128.8, 127.1, 117.0, 82.1, 60.4, 52.6, 51.4, 41.2, 32.4, 28.1, 25.0, 22.8, 21.7

MS (EI): 364 (M-56)$^+$, 336, 320, 219, 164, 120

HRMS (FAB) $C_{22}H_{32}N_2O_6$ calcd for (M+Na)$^+$ 443.2158, found 443.2145

EXAMPLE 5

2-Oxo-13-tridecanolide (45a) [also named 2,3-dione-oxacyclotetradecane]:

A highly dilute solution of cyano keto phosphorane 33a (40 mg, 0.08 mmol) in 150 mL of $CH_2Cl_2$ was treated with ozone at −78° C. until the color of the solution remained blue. The mixture was then purged with $N_2$ to colorless. The clear solution was then stirred overnight at room temperature. The solvent was evaporated and the residue was chromatographed over silica gel, eluting with $CH_2Cl_2$ to afford the α-keto ester 45a (8 mg, 0.035 mmol) in 43% yield.

$R_f$ 0.35 in $CH_2Cl_2$

IR (film) 1750, 1720, 1460, 1280 $cm^{-1}$ $^1$H NMR (300 MHz, $CDCl_3$) δ 4.35 (t, J=5.3 Hz, 2H, $CH_2$), 2.7 (t, J=7.1 Hz, 2H, $CH_2$), 1.8-1.2 (m, 18H)

GC-MS: 226 (M$^+$), 139, 125, 111, 98, 83

HRMS (EI) calcd for $C_{13}H_{22}O_3$ (M$^+$) 226.1569, found 226.1556

EXAMPLE 6

Methyl ω-Carbobenzyloxyamino-α-ketotridecanoate (23) [also named 2-oxo-13-[[(phenylmethoxy)carbonyl]amino] tridecanoic acid, methyl ester]:

A solution of cyano keto phosphorane 22 (600 mg, 0.95 mmol) in 40 mL of (7/3) $CH_2Cl_2$/MeOH was treated with ozone at −78° C. until the color of the solution remained blue. The mixture was then purged with $N_2$ to colorless at room temperature. The solvent was evaporated and the residue was chromatographed over silica gel, eluting with (3/1)-hexanes/EtOAc to afford the α-keto ester 23 (304 mg, 0.79 mmol) in 83% yield as a white solid.

$R_f$ 0.64 (1/1) EtOAc-hexanes mp 60°−61° C.

IR (film) 3330, 1730, 1705, 1680, 1540, 1260 $cm_{-1}$ $^1$H NMR (300 MHz, $CDCl_3$) δ 7.33 (br s, 5H, Ph), 5.07 (s, 2H, CH2Ph), 5.07 (br s, 1H, NH), 3.84 (s, 3H, OMe), 3.17 (m, 2H, CH2), 2.81 (t, J=7.3 Hz, 2H, CH2), 1.7-1.2 (m, 18H)

$^{13}$C NMR (75 MHz, $CDCl_3$) δ 194.3, 161.6, 156.3, 136.7, 128.5, 128.0, 66.5, 52.8, 41.1, 39.3, 29.9, 29.4, 29.3, 29.2, 28.9, 26.7, 22.9

MS (CI) 392 (M+1)$^+$, 368, 332, 314, 285, 256, 224, 197

HRMS (CI) calcd for $C_{22}H_{34}NO_5$ (M+1)$^+$ 392.2437, 392.2443

EXAMPLE 7

2-keto-3-N(tertbutoxycarbonyl)-4-phenylbutanoate (25):

A solution of cyano keto phosphorane 24 (200 mg, 0.37 mmol) in 4 mL of (7/3) CH2Cl2-MeOH was treated with $O_3$ at −78° C. until the color of the solution remained blue. The mixture was then purged with $N_2$ at −78° until the blue color faded. After removal of the solvent, the residue was purified by flash chromatography over silica gel, eluting with (3/1) hexanes-EtOAc to get the product 25 (100 mg, 0.33 mmol) in 89% yield as an oil.

$R_f$ 0.48 (1/1.5) EtOAc-hexanes

[α]$_D$+32° (c 2.6, $CHCl_3$)

IR (neat) 3380, 1750-1700 (br), 1500, 1370, 1280, 1250, 1050 $cm^{-1}$ $^1$H NMR (300 MHz, $CDCl_3$) δ 7.32-7.14 (m, 5H, Ph), 5.18 (m, 1H, CH), 5.04 (d, J=6.7 Hz, 1H, NH), 3.87 (s, 3H, OMe), 3.22 (dd, J=13.9, 5.6 Hz, 1H, CH$_2$Ph), 3.20 (dd, J=13.9, 6.8 Hz, 1H, CH$_2$Ph), 1.40 (s, 9H, Bu)

$^{13}$C NMR (75 MHz, CDCl$_3$) δ 192.3, 160.8, 155.0, 135.2, 129.3, 128.7, 127.2, 80.3, 57.7, 53.0, 37.0, 28.1

HRMS (FAB) C$_{16}$H$_{21}$NO$_5$ calcd for (M+Na)$^+$ 330.1317; found 330.1344

EXAMPLE 8

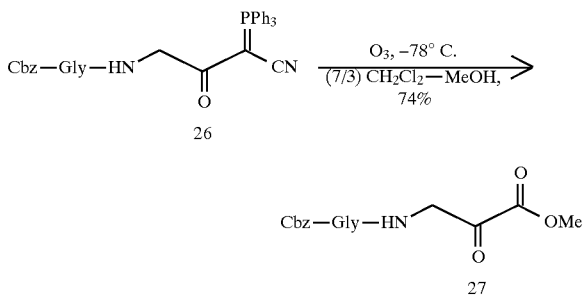

26

27

1-Methyl 2-Keto-3-N(carbobenzyloxyglycyl)-propanoate (27) [also named 2-oxo-3-[[[[(phenylmethoxy)carbonyl]amino]acetyl]amino]-propanoic acid, methyl ester]:

A solution of cyano keto phosphorane 26 (100 mg, 0.18 mmol) in 2 mL of (7/3) CH$_2$Cl$_2$-MeOH was treated with O$_3$ at −78° C. until the color of the solution remained blue. The mixture was then purged with N$_2$ at −78° C. until the blue color faded. After removal of the solvent, the residue was triturated with (5/4) benzene-hexanes and the white solid was collected to get the product 27 (41 mg, 0.14 mmol) in 74% yield. mp 97°–99° C.

IR (film) 3420, 3300, 1750-1700 (br), 1500, 1250-1200 cm$^{-1}$ $^1$H NMR (300 MHz, CDCl$_3$) δ 7.34 (br s 5H, Ph), 6.55 (br s, 1H, NH), 5.35 (br s 1H, NH), 5.13 (s, 2H, PHCH$_2$), 4.60 (d, J=4.9 Hz, 2H, CH$_2$), 3.93 (d, J=5.9 Hz, 2H, CH$_2$), 3.90 (s, 3H, OMe)

Analysis calcd for C$_{14}$H$_{16}$N$_2$O$_6$: C 54.53, H 5.23, N 9.09; found C 54.34, H 5.23, N 9.06

EXAMPLE 9

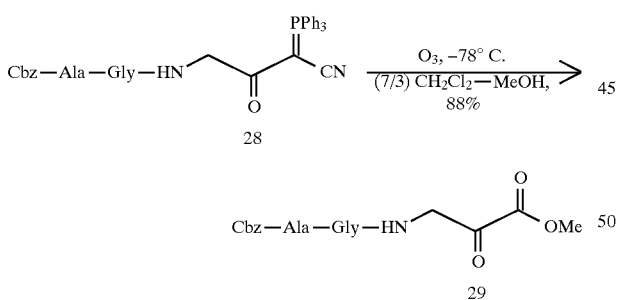

28

29

Methyl Ester of α-Keto Acid Derived from Cbz-ala-gly-gly-OH (29):

A solution of cyano keto phosphorane 28 (100 mg, 0.16 mmol) in 2 mL of (7/3) CH$_2$Cl$_2$-MeOH was treated with O$_3$ at −78° C. until the color of the solution remained blue. The mixture was then purged with N$_2$ at −78° C. until the blue color faded. After removal of the solvent, the residue was triturated with (5/4) benzene-hexanes and the solvent was decanted to get the product 29 (41 mg, 0.14 mmol) in 88% yield as a white solid. mp 70°–72° C.

[α]$_D$ −9.5° (c 1.2, CHCl$_3$)

IR (film) 3420, 3300, 1750-1650 (br), 1500, 1250-1200 cm$^{-1}$ $^1$H NMR (300 MHz, CDCl$_3$) δ 7.3-7.2 (m, 5H, Ph), 6.95 (br s 1H, NH), 6.81 (br s, 1H, NH), 5.29 (d, J=6.0 Hz, 1H, NH), 5.10 (d, AB, J=12.0 Hz, 1H, 1/2 CH$_2$Ph), 5.09 (d, AB, J=12.0 Hz, 1H, 1/2 CH$_2$Ph), 4.52 (d, J=5.3 Hz, 2H, CH$_2$), 4.19 (m, 1H, CH), 3.99 (br s, 2H, CH$_2$), 3.88 (s, 3H, OMe), 1.40 (d, J=7.1 Hz, 3H, Me)

HRMS (FAB) calcd for C$_{17}$H$_{21}$N$_3$O$_7$ (M+1)$^+$ 380.1457, found 380.1415

Analysis calcd for C$_{17}$H$_{21}$N$_3$O$_7$: C 53.81, H 5.58, N 11.08; found C 53.32, H 5.64, N 10.76

EXAMPLE 10

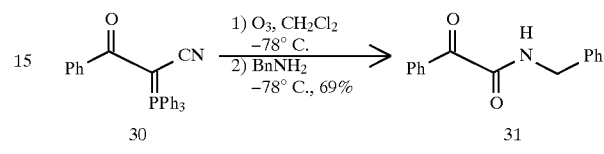

30

31

N-benzyl-benzoylformamide (31):

A solution of cyano keto phosphorane 30 (200 mg, 0.49 mmol) in 5 mL of CH$_2$Cl$_2$ was treated with ozone at −78° C. until the color of the solution remained yellow-blue. The mixture was then purged with N$_2$ at −78° C. until the blue color faded. To this yellow solution was added slowly benzyl amine (63 mg, 0.59 mmol) and the resulting solution was stirred at −78° C. for 1 hour. After warming up to room temperature, the solvent was evaporated and the residue was purified by flash chromatography over silica gel, eluting with CH$_2$Cl$_2$ to afford the α-keto amide 31 (82 mg, 0.34 mmol) in 69% yield as a pale yellow solid.

R$_f$ 0.44 (1/3) EtOAc-hexanes mp 90°–91° C.

IR (film) 3250, 1675, 1640, 1570, 1450, 1425, 1220 cm$^{-1}$ $^1$H NMR (300 MHz, CDCl$_3$) δ 8.35 (m, 2H, Ph), 7.26 (br t, 1H, Ph), 7.47 (br t, 2H, Ph), 7.33 (m, 5H, Ph), 4.56 (d, J=6.0 Hz, 2H, CH$_2$Ph)

$^{13}$C NMR (75 MHz, CDCl$_3$) δ 187.5, 161.6, 137.1, 134.4, 133.3, 131.2, 128.8, 128.5, 127.9, 43.5

GC-MS 239 (M$^+$), 105, 91

HRMS (CI) calcd for C$_{15}$H$_{14}$NO$_2$ (M+1)$^+$ 240.1024, found 240.1036

EXAMPLE 11

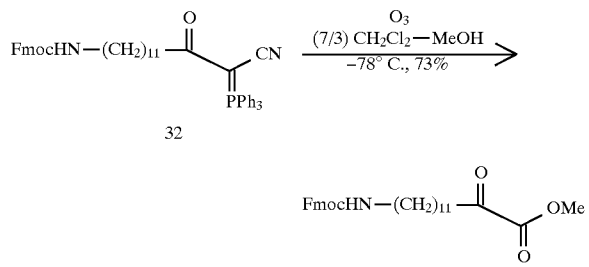

32

33

Methyl α-Keto-ω-(FMOC-amino)tridecanoate (33):

A solution of cyano keto phosphorane 32 (300 mg, 0.42 mmol) in 5 mL of (7/3) CH$_2$Cl$_2$-MeOH was treated with O$_3$ at −78° C. until the color of the solution remained blue. The mixture was then purged with N$_2$ at −78° C. until the blue color faded. After removal of the solvent, the residue was purified by flash chromatography over silica gel, eluting with (30/1) CH$_2$Cl$_2$-EtOAc to get the α-keto ester 33 (146 mg, 0.30 mmol) in 73% yield as a white solid.

R$_f$ 0.71 (1/1) EtOAc-hexanes mp 80°–81° C.

IR (film) 3440, 2905, 1720, 1510, 1445 cm$^{-1}$ $^1$H NMR (300 MHz, CDCl$_3$) δ 7.60-7.26 (m, 8H, Ph), 4.72 (m 1H, NH), 4.38 (br d, J=6.9 Hz, 2H, CH$_2$O), 4.20 (br t, J=6.7, 1H, CHCH$_2$), 3.84 (s, 3H, OMe), 3.17 (m, 2H, NCH$_2$), 2.81 (t, J=7.3 Hz, 2H, CH$_2$), 1.6-1.2 (m, 18H)

$^{13}$C NMR (75 MHz, CDCl$_3$) δ 194.1, 161.4, 156.3, 143.9, 141.1, 127.4, 126.8, 124.9, 119.8, 66.3, 52.7, 47.1, 40.9, 39.1, 29.8, 29.3, 29.2, 29.1, 28.7, 26.6, 22.7

HRMS (FAB) C$_{29}$H$_{37}$NO$_5$ calcd for (M+Na)$^+$ 502.2569; found 502.2555

EXAMPLE 12

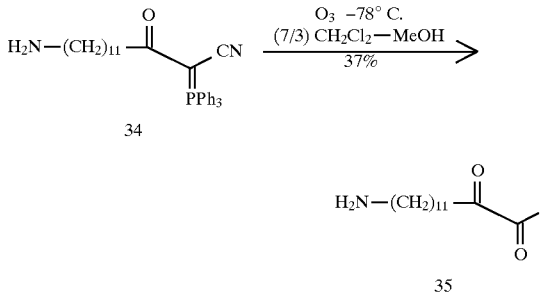

Methyl α-keto-ω-nitrotridecanoate (35):

A solution of ω-amino ylide (34) (70 mg, 0.14 mmol) in 15 mL of CH$_2$Cl$_2$/MeOH (7:3) was treated with ozone at −78° C. until the color of the solution remained blue. The mixture was then purged with N$_2$ to colorless. The solvent was removed and the residue was purified by flash chromatography over silica gel, eluting with pure CH$_2$Cl$_2$ to give the product 35 (15 mg, 0.05 mmol) in 37% yield.

R$_f$ 0.42 in (3/1) hexanes-EtOAc

IR (neat) 1730, 1550, 1470, 1430, 1390, 1280 cm$^{-1}$ $^1$H NMR (300 MHz, CDCl$_3$) δ 4.35 (t, J=7.1 Hz, 2H, O$_2$NCH$_2$), 3.84 (s, 3H, OMe), 2.81 (t, J=7.3 Hz, 2H, CH$_2$), 1.98 (m, 2H, CH$_2$), 1.61 (m, 2H, CH$_2$), 1.25 (m, 14H)

$^{13}$C NMR (75 MHz, CDCl$_3$) δ 194.3, 161.8, 75.7, 52.8, 39.3, 29.3, 29.25, 29.2, 28.9, 28.8, 27.4, 26.2, 23.0

MS (CI) 288 (M+1)$^+$, 228, 181, 163

HRMS (FAB) C$_{14}$H$_{25}$NO$_5$ calcd (M+Na)$^+$ 310.1630; found 310.1642

EXAMPLE 13

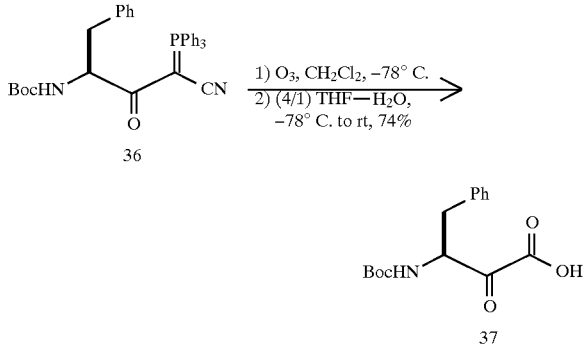

α-Keto Acid Derived from N-Boc-phenylalanine (37):

A solution of cyano keto phosphorane 36 (200 mg, 0.37 mmol) in 8 mL of CH$_2$Cl$_2$ was treated with O$_3$ at −78° C. until the color of the solution remained yellow-blue. The mixture was then purged with N$_2$ at −78° C. To this yellow solution was added slowly (4/1) THF-H$_2$O (10 mL) and the mixture was allowed to warm up to room temperature gradually. After stirring at room temperature for 2 hours, the organic solvent was evaporated and the residue was taken up with 1N NaOH (20 mL at 0° C. and washed with EtOAc. The aqueous layer was acidified by 3N HCl to pH 2–3 and then extracted with EtOAc. The organic layer was washed with brine, dried over Na$_2$SO$_4$, filtered and concentrated to get the product 37 (79 mg, 0.27 mmol) in 74% yield as a gummy solid.

IR (CHCl3) 3430, 3500-3300 (br), 2980, 1800-1650 (br), 1505, 1370, 1170 cm$^{-1}$ $^1$H NMR (300 MHz, CDCl$_3$) δ 7.3-7.1 (m, 5H, Ph), 6.64 (m, 1H, NH), 4.69 (m, 1H, CH), 3.15 (dd, J=13.7, 3.0 Hz, 1H 1/2 CH$_2$Ph), 2.65 (dd, J=13.7, 10.0 Hz, 1H, 1/2 CH$_2$Ph), 1.29 (s, 9H, $^t$Bu)

$^{13}$C NMR (75 MHz, CDCl$_3$) δ 193.6, 161.8, 155.6, 136.0, 135.2, 129.4, 128.7, 128.6, 128.4, 127.1, 127.0, 81.0, 80.5, 57.5, 54.3, 37.7, 36.8, 28.2, 28.2 (two conformers)

MS (EI) 236 (M-Bu)$^+$, 175, 120, 97, 91, 59

The relevant portions of all cited patents, patent applications and other publications are specifically incorporated herein by reference.

The scope of the following claims is intended to encompass all obvious changes in the details, materials and arrangement of parts that will occur to one of ordinary skill in the art.

We claim:

1. A method for making a ketone containing compound comprising the steps of (A) reacting a (cyanomethylene)triphenylphosphorane with a carbonyl containing compound selected from the group consisting of carboxylic acid of formula RCOOH, acid anhydride derived therefrom or acyl chloride of formula RCOCl, wherein R is a structural diversity element selected from the group consisting from alkyl, cycloalkyl, substituted and unsubstituted aryl, heteroaryl, peptidyl, heteroatom-substituted alkyl and cycloalkyl, to make the corresponding cyano keto phosphorane;

(B) oxidizing said cyano keto phosphorane to make an α-ketoacyl cyanide; and (C) reacting said α-ketoacyl cyanide with a nucleophile of formula NuH wherein NuH is a structural diversity element selected from the group consisting of amine, amino acid, peptidyl residue, water, H$_2$S, alcohol and thiol, to form a ketone-containing compound.

2. The method of claim 1, wherein the ketone containing compound which is formed is an α-keto acid, ester or amide.

3. The method of claim 1 which further comprises preparing a plurality of different ketone containing compounds for use in generating a spatially arranged array or a combinatorial library.

4. The method of claim 3 which further comprises generating a combinatorial library from the plurality of different ketone containing compounds.

5. The method of claim 2 which further comprises preparing a plurality of different α-keto acid, ester or amide compounds for use in generating a spatially arranged array or a combinatorial library.

6. The method of claim 5 which further comprises generating a combinatorial library from the plurality of different α-keto acid, ester or amide compounds.

* * * * *

UNITED STATES PATENT AND TRADEMARK OFFICE
CERTIFICATE OF CORRECTION

PATENT NO. : 5,834,588
DATED : November 10, 1998
INVENTOR(S) : Harry Wasserman, Wen-Bin Ho It is certified that error appears in the above-identified patent and that said Letters Patent is hereby corrected as shown below:

Column 1, line 5, insert the following,

The invention identified above is a subject invention under 35 U.S.C. 200, et seq., and the Standard Patent Rights Clause at 37 C.F.R. 401.14 or F.A.R. 52.227-11, which are included among the terms of the above-identified grant/contract award from the Public Health Service/National Institutes of Health.

Signed and Sealed this

Twenty-fifth Day of May, 1999

Attest:

Q. TODD DICKINSON

*Attesting Officer*

*Acting Commissioner of Patents and Trademarks*